United States Patent [19]

Kreuwel

[11] Patent Number: 6,100,966
[45] Date of Patent: Aug. 8, 2000

[54] TEST DEVICE FOR BODILY FLUIDS

[75] Inventor: Hermanus Johannes Maria Kreuwel, Schijndel, Netherlands

[73] Assignee: Akzo Nobel N.V., Arnhem, Netherlands

[21] Appl. No.: 09/297,596

[22] PCT Filed: Oct. 23, 1997

[86] PCT No.: PCT/EP97/05984

§ 371 Date: May 4, 1999

§ 102(e) Date: May 4, 1999

[87] PCT Pub. No.: WO98/20322

PCT Pub. Date: May 14, 1998

[30] Foreign Application Priority Data

Nov. 4, 1996 [EP] European Pat. Off. ............ 96203057

[51] Int. Cl.$^7$ .................................................. G01N 1/00
[52] U.S. Cl. ............................. 356/36; 356/39; 356/244
[58] Field of Search .......................... 356/36, 244, 39

[56] References Cited

U.S. PATENT DOCUMENTS 5,131,756  7/1992  Schmidt et al. ...................... 356/446

FOREIGN PATENT DOCUMENTS

| 0394909 | 10/1990 | European Pat. Off. . |
| 0654661 | 5/1995 | European Pat. Off. . |
| 3426335 | 1/1986 | Germany . |
| 9213278 U | 12/1992 | Germany . |

Primary Examiner—Robert H. Kim
Assistant Examiner—Phil Natividad
Attorney, Agent, or Firm—Gregory R. Muir

[57] ABSTRACT

A test device for bodily fluids comprising a solid carrier with a bonded reagent, a light source and a light detector. Light source and light detector are positioned is such a way that the majority of the light travels within the porous body along a transmission path, which is determined by scattering or reflection of the light within the porous body, until it arrives at the exit end where the transmitted light is measured.

6 Claims, 3 Drawing Sheets

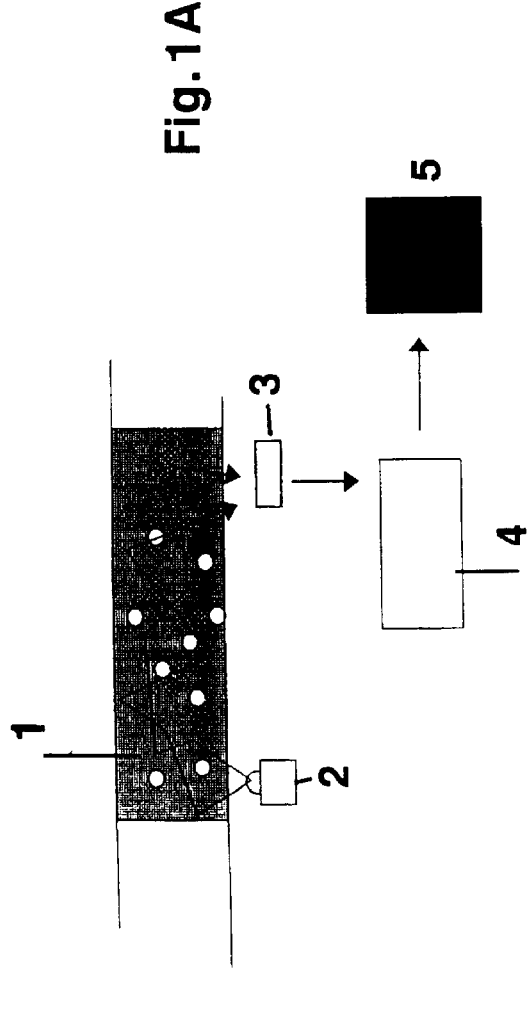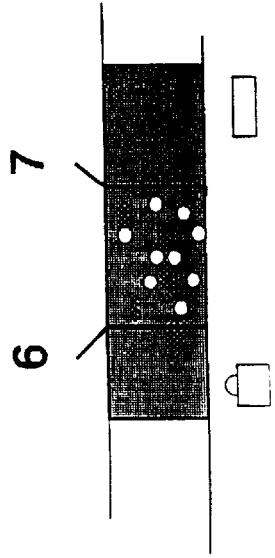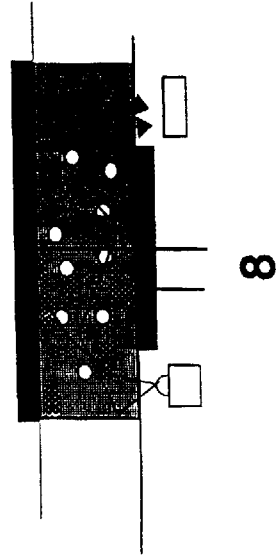

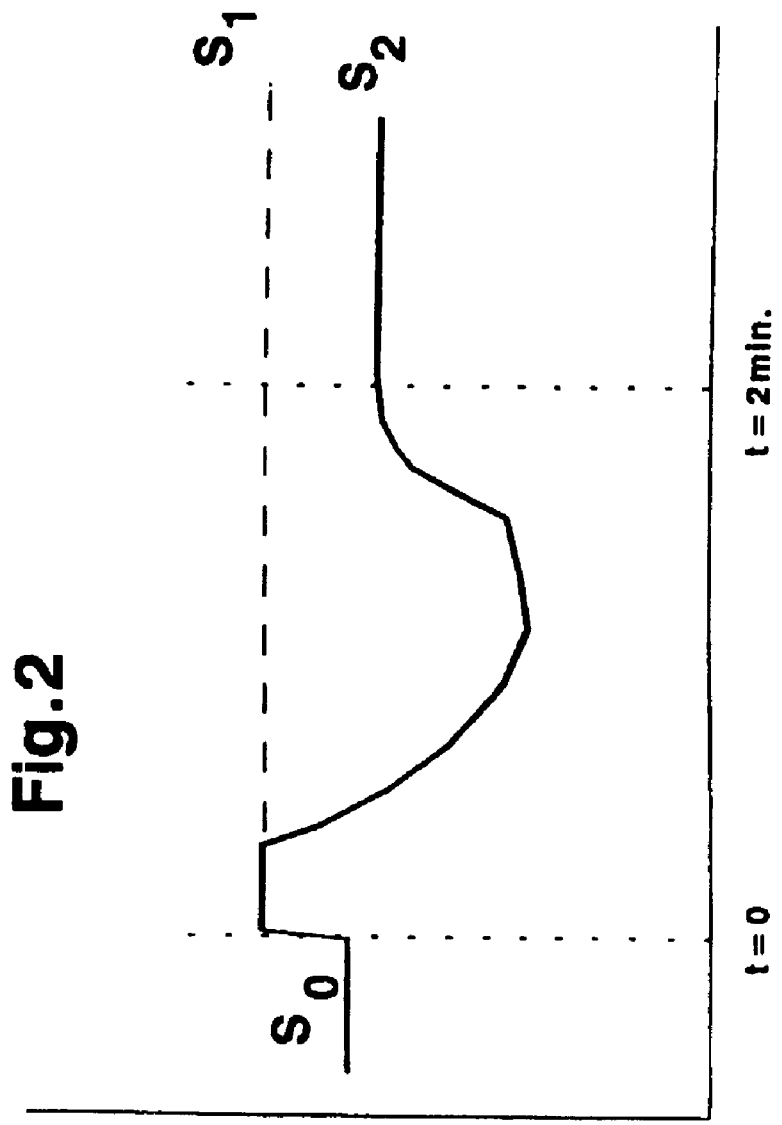

TEST DEVICE FOR BODILY FLUIDS

BACKGROUND OF THE INVENTION

The invention relates to a test device for bodily fluids comprising a solid carrier with a bonded reagent, a light source for transmitting light to the carrier and a light detector for detecting light received from the carrier.

Such test devices are well known in the art. U.S. Pat. No. 5,131,756 discloses a test carrier analysis device for determining the reflectivity of a test field surface. An optical unit of the device contains several light transmitters and a measurement receiver, whereby the light transmitters are directed obliquely from above onto the measurement surface. The light transmitters are arranged opposite to one another with off-set planes of incidence.

Other test devices known in the art employ light sources wherein the light impinges on the measurement surface uniformly from all directions in space. Commonly, the light sources that are used are light-emitting diodes, which are favoured in view of their low-energy use, low costs and high reliability.

Test devices to which the invention relates are particularly useful for pregnancy tests but are not confined hereto. A prime consideration with these test devices is that they must be small, manageable and cheap to manufacture in view of the required suitability for self-diagnosis by a user.

The problem with known devices is the lack of accuracy, particularly in the area where the signals measured by the detector do not warrant an unambiguous positive or negative test result.

SUMMARY OF THE INVENTION

The test device according to the invention aims to provide a cheap, reliable and accurate test device suitable for both home- and professional use. The test device according to the invention is therefore characterized in that in use the light source transmits light to the carrier in a direction suitable to cause the substance of the light to enter the carrier. Contrary to any test device known in the art, the test device according to the invention is not based on the reflection of light transmitted to a carrier-surface by the detector, but is based on a quite distinct principle; i.e. the test device according to the invention realises a prolonged path for the light imparted in the carrier's interior for travelling to the detector. Along that path in the interior of the carrier the light is scattered and diffused allowing for an increased interaction through absorption of the light by such area of the carrier where a sample of bodily fluid has entertained a reaction with the reagent bonded in the carrier. Due to this measure the sensitivity and accuracy for measuring the occurrence and the extent of any such reaction is highly increased. This is particularly supported by assuring that in use the substance of the light received by the detector is received from the carrier.

A further increased sensitivity of the test device can be accomplished by covering the carrier at least partly by a reflective foil or coating. The coating may be provided on one side or on all sides, but in all cases it is required that the carrier is at least partly covered by a reflective foil or coating and that this reflective foil or coating is locally absent near the light source and the detector, to allow light to travel to and from the carrier.

The reaction of the carrier bonded reagent with the sample of bodily fluid, is particularly supported when the carrier is porous, providing therewith a large surface/volume ratio so that an effective reaction within a confined area is enabled, and the effective propagation of light through the carrier is promoted. Very suitable materials for the carrier can be selected from the group comprising silica paper, polyethylene, nitrocellulose, glass beads, etc.

Practice has shown that the distance between light source and detector can be kept at a moderate value in the range of 1–5 mm. The sensitivity of the test device for the light transmitted by the light source is improved by the application of blocking means to prevent the light to travel directly from the light source to the detector. In practice, the application of such blocking means improves the yield at the detector by a factor 2. A feasible solution is to vary the position of light source and detector such that the light transmitting and light receiving surfaces are not in the same plane. Preferably, and most simply, the blocking means are, however, formed as a light shield, such as a shield of material which is not translucent. It is advantageous that the test device further comprises an arithmetic logic unit connected with the light source and the detector for controlling the emittance and duration of emittance of light by the light source and the processing of signals measured by the detector. This allows for automatic and controlled use of the test device with high immunity against false operation.

It is desirable then that the arithmetic logic unit monitors and controls the beginning and ending of a test-run, and calculates a test-value in dependence of the signals measured by the detector in relation to a reference value.

The automatic determination of the test value as provided by the invention circumvents the subjective interpretation which follows from other conventional test methods known in the art such as those employing dipsticks. Dipsticks require a visual detection by the naked eye to see whether a detection reaction has occurred.

A further advantageous embodiment of the test device according to the invention is characterised in that the arithmetic logic unit includes a memory containing a typical signal-trajectory measured by the detector during a regular test-run, and that the arithmetic logic unit monitors the trajectory of the signals actually measured by the detector during a test run and compares same with the said signal-trajectory contained in the memory, and calculates and releases a test-value in dependence of the difference between the typical and the actual trajectory of the signal being less than a predetermined value. This further improves the accuracy and reliability of the test.

BRIEF DESCRIPTION OF THE DRAWINGS

The invention shall now further be elucidated with reference to the enclosed drawings in which:

FIG. 1a shows a schematic drawing of a first embodiment of test device according to the invention;

FIG. 1b hows a schematic drawing of a second embodiment of the test device according to the invention;

FIG. 1c shows a schematic drawing of a third embodiment of the test device according to the invention;

FIG. 2 shows a typical signal-trajectory measured by the detector during test run and;

DETAIL DESCRIPTION OF THE INVENTION

Figure 3:
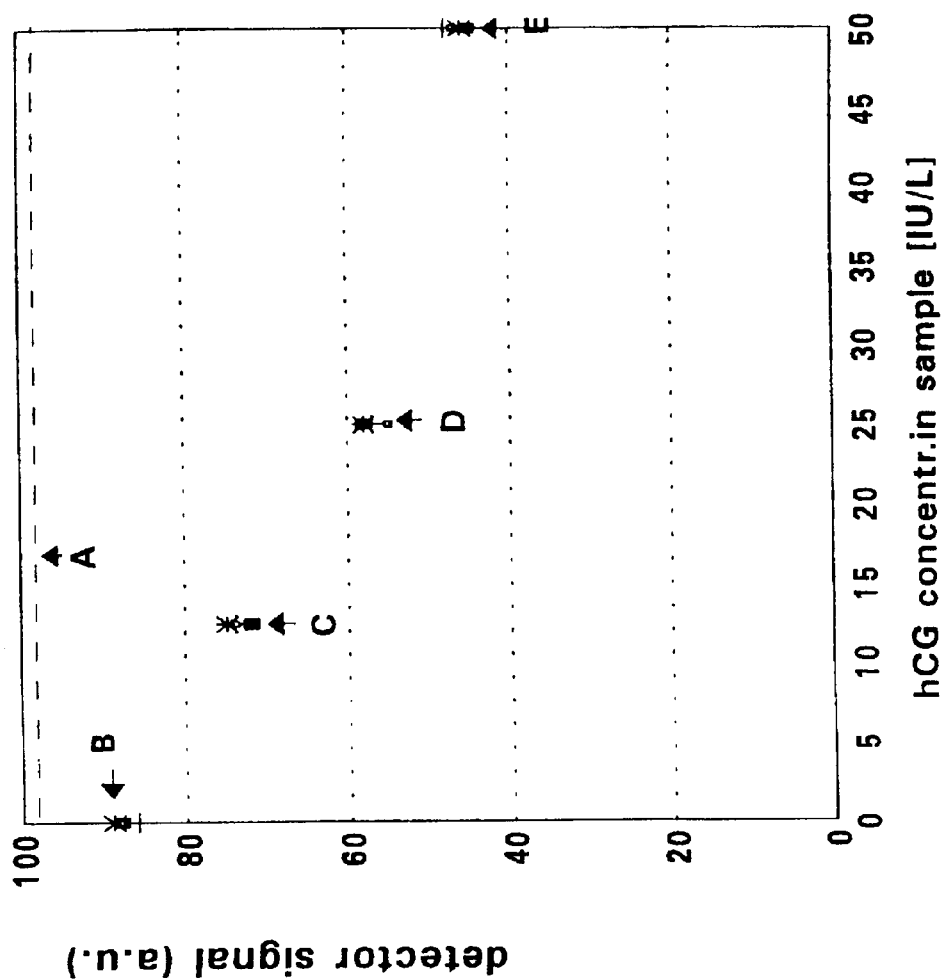
FIG. 3 shows some results realised by the test device according to the invention when used in a pregnancy test.

FIG. 1a shows the basic detection principle of the invention in which a porous body 1 is used as a carrier of an immobilised specific binding reagent. The porous body 1 may consist of silica paper, polyethylene, nitrocellulose, glass beads or another suitable material. When used for a pregnancy test, a sample of urine which may carry an analyte which is to be detected, is mixed with a conjugate that is labelled with a light-absorbing component such as a particle showing characteristics that are detectable due to its interference with the analyte as will be explained below. When the sample of urine containing the analyte flows through the porous body 1, at least a fraction of the label contained in the conjugate is immobilised within the porous body 1 due to a reaction with the reagent in the porous body 1. A light source 2, for instance a light emitting diode, transmits light to the porous body 1 in a direction suitable to cause the substance of the light to enter the porous body 1. The light travels then within the porous body 1 along a transmission path which is determined by scattering or reflection of the light within the carrier body until it arrives at the exit end, where the detector 3 is located. There is no direct visibility between the light emitting diode 2 and the detector 3, nor is it desired to have light reach the detector 3 via reflection on the surface of the carrier body 1. The substance of the light received by the detector 3 is departed therefore from the carrier 1. Due to the part absorption of the light originating from the light emitting diode 2 by the part of the light absorbing component that is immobilized in the porous body 1, the light received by the detector 3 is a fraction thereof, the magnitude of which is measurable.

FIG. 1b shows a second embodiment of the test device in which the porous body 1 is only partly provided with an area with the immobilised bounding reagent. The area with the reagent is provided between the dotted lines indicated with reference numerals 6 and 7.

FIG. 1c shows a third preferred embodiment of the test device according to the invention wherein the porous body 1 is covered by a reflective foil or coating 8 on all parts of the porous body 1, except for the area where light is to travel to and from the porous body 1.

In a preferred embodiment of the test device according to the invention, the device further comprises an arithmetic logic unit 4, as shown in FIG. 1a, which is connected to the light source 2 and the detector 3 for controlling the emmitance and duration of emmitance of light by the light source 2 and the processing of signals measured by the detector 3. An indicator S is connected to the arithmetic logic unit 4 to display the test results.

FIG. 2 shows a typical test signal as processed by the arithmetic logic unit 4. The test does not start until detector 3 measures and signals to the arithmetic logic unit 4 an increase in the amount of detected light; see the change of level So to S1 in FIG. 2. This resets a time counter to t=0. Initially, a sample of urine brought into the test device may be void of any labelled reagent due to which the output of detector 3 is maintained on a high level S1. The sample further propagates through the carrier 1, due to which the level of light detected by detector 3 decreases until it reaches a lower limit, rises again and arrives at a steady state value S2, which counted from the start of the test t=0, takes about two minutes. When reaching the steady state value, the test is deemed completed and the arithmetic logic unit 4 calculates the test result in dependence of the level S2 as measured by the detector 3 in relation to a reference value S1, which in this case corresponds to a sample of unlabelled urine.

Preferably, the arithmetic logic unit 4 monitors the beginning and ending of a test-run, and calculates a test-value in dependence of the signals measured by the detector 3 in relation to the reference-value S1. FIG. 3 shows some experimental results using a hyperred light emitting diode 2 as a light source. Carbon particles were used as a label contained in the conjugate that was mixed with the bodily fluid to be measured by the test device according to the invention. The carrier body 1 was made of silica paper, with thickness 0.7 mm, width 4 mm and length 10 mm. The volume of the coated area within this carrier was 1 mm$^3$. The test device was used to measure the hCG concentration in a sample of urine. The concentration of hCG is set forth on the X-axis in units per liter; the Y-axis shows the signal as detected by detector 3. The total test time for each sample was 2 minutes 30 seconds. A reference line A shows the detection level corresponding to a clear urine sample being measured void of hCG and conjugate. A first sample, indicated by arrow B, corresponds with a hCG concentration of 0 units per liter, however, with the employment of conjugate. Arrows C, D and E refer to further test results corresponding to hCG concentrations of 12.5, 25 and 50 units per liter respectively. From these measurements it is evident that the test device according to the invention is highly sensitive to any measured differences in concentration of the analyte to be detected, showing only moderate variations in the measured value detected by detector 3 with repeated measurements. The accuracy of the test device according to the invention assures therefore a high reliability of the test results.

What is claimed is:

1. A diagnostic device for the detection of an analyte in a bodily fluid, comprising a light source (2), a porous carrier (1) with a bonded reagent capable of reacting with an analyte and light detector (3), arranged in such a way that light emitted from the light source may enter into the porous structure of the carrier, travel through the carrier and exit the carrier at a position suitable to be detected by the detector, and the light absorbing properties of the carrier are altered dependent on the analyte concentration when the bodily fluid containing the analyte enters the carrier, wherein the light detector is arranged in such a way that it cannot receive light either directly from the light source or light which is reflected from the surface of the porous carrier, but instead can receive light that has travelled a prolonged path through the porous structure of the carrier.

2. The diagnostic device according to claim 1, wherein the porous carrier is at least partially covered by a reflective foil or coating (8).

3. The diagnostic device according to claim 1, wherein the porous carrier is selected from the group consisting of silica paper, polyethylene, nitro-cellulose, and glass beads.

4. The diagnostic device according to claim 1, wherein the distance between light source and detector is in the range of 1–5 mm.

5. The diagnostic device according to claim 1, additionally comprising a blocking means which functions as a light shield in order to prevent light from travelling directly from the light source to the detector.

6. The diagnostic device according to claim 1, further comprising an arithmetic unit functionally connected with the light source and the detector in order to control the emission and duration of the emission of light and to receive and process signals measured by the detector.

* * * * *